United States Patent [19]

Newkirk et al.

[11] Patent Number: 4,927,420

[45] Date of Patent: May 22, 1990

[54] ULTRA-SHARP TUNGSTEN NEEDLE FOR ELECTROSURGICAL KNIFE

[75] Inventors: John B. Newkirk, Evergreen, Colo.; Kim H. Manwaring, Scottsdale, Ariz.

[73] Assignee: Colorado Biomedical, Inc., Evergreen, Colo.

[21] Appl. No.: 271,235

[22] Filed: Nov. 14, 1988

[51] Int. Cl.$^5$ ............................................. A61B 17/36
[52] U.S. Cl. ......................................... 606/45; 606/49
[58] Field of Search .................... 128/303.13–303.18, 128/329 A, 339; 606/41, 45, 49

[56] References Cited

U.S. PATENT DOCUMENTS

| | | | |
|---|---|---|---|
| 3,976,078 | 8/1976 | Toriello | 128/329 A |
| 4,593,691 | 6/1986 | Lindstrom et al. | 128/303.15 |
| 4,708,137 | 11/1987 | Tsukagoshi | 128/303.17 |
| 4,785,807 | 11/1988 | Blanch | 128/303.17 |

*Primary Examiner*—Max Hindenburg
*Attorney, Agent, or Firm*—Beaton & Swanson

[57] ABSTRACT

A method and apparatus for performing electrosurgery with an ultra-sharp electrode composed of a refractory alloy, said electrode having a blunt end and a tip end, and a method for forming the ultra-sharp electrode by rotating about its axis a vertically held cylindrical rod composed of a refractory alloy and repeatedly withdrawing and replacing the rod into a pool of molten oxidizing agent.

13 Claims, 1 Drawing Sheet

ULTRA-SHARP TUNGSTEN NEEDLE FOR ELECTROSURGICAL KNIFE

BACKGROUND OF THE INVENTION

Electrosurgery is a form of surgery in which body tissue is cut or cauterized by a high frequency current. A variety of electrosurgical tools have been employed. In monopolar adaptations, a radio frequency (RF) signal is transmitted to an electrosurgical electrode. When employing this type of electrosurgical device, a "patient plate" is placed upon the patient's skin outside of the surgical field, with the plate being connected back to the RF signal generator to ground the patient. The current from the generator thus completes its circuit when the electrode of the electrosurgical device comes close to or in contact with the patient's body. The small point of approach or contact between the body and the electrosurgical device creates an intense current localized so that a cutting action may occur. Since the contact area between the patient and the patient plate is so large, the current is not localized and the current flow does not harm the patient.

In bipolar adaptations, an RF generator transmits current to an electrosurgical device that contains two electrodes one of which conducts the current back to the generator to complete the circuit. A small gap exists between the two conductive elements in the device between which the current flows. The flowing current between the two electrodes provides the heat for cutting or for coagulation of bleeding sites.

The electrosurgical electrode has been maintained for many years in a wide variety of shapes such as needles for delicate cutting, or a wire loop for scraping. In addition, electrosurgical electrodes shaped as spatulas have been used in normal surgical cutting like a scalpel. Although most electrosurgical electrodes are composed of stainless steel, some are composed of alloys containing primarily tungsten, molybdenum, chromium, nickel or cobalt.

When in a cutting mode, the current created when a conventional electrosurgical electrode touches the body tissue incises the tissue. The heat created by the current occasionally penetrates deeply enough into the adjoining tissue so as to cause delayed healing and excessive scar formation. By varying the mode of the RF generator output, it is also possible to utilize the electrosurgical device to enhance cauterization or coagulation of blood in a wound. In the cauterizing mode, the electrosurgical electrode generates much more heat than when in the cutting mode.

Although offering certain advantages to conventional knife dissection, electrosurgical devices currently available suffer from several drawbacks. The relatively high current required causes occasional "sparking" of the current between the electrode and the body tissue when in the cutting mode. Such action causes localized hot spots that tend to smoke and give off a strong odor, as well as to create unnecessary tissue damage. When used in the cauterization mode, the high power required can often generate enough heat to melt the tip of stainless steel needle electrodes and destroy its sharpness.

U.S. Pat. Nos. 4,688,569 of Rabinowitz and 4,545,375 of Cline both describe monopolar electrosurgical electrode holder devices. Both of these contemplate the use of electrode needles for cutting and cauterizing and suggest the use of tungsten needles. The tungsten needles of these patents are machined and do not have the highly beneficial ultra-sharp tip of the present invention. U.S. Pat. No. 3,768,482 of Shaw describes a bipolar electrosurgical device resembling a scalpel.

This invention relates to an improved electrosurgical electrode and methods for utilizing and producing such superior electrosurgical electrodes. The invention encompasses the use of an "ultra-sharp" refractory alloy needle as an electrosurgical electrode, the method for manufacturing such device as well as the actual ultra-sharp needle itself.

Although ultra-sharp refractory alloy needles are known in the prior art, particularly in the field of electron microscopy, the surprising benefits obtained when employed as an electrosurgical electrode were quite unanticipated. Use of the ultra-sharp needle as an electrosurgical electrode allows for the use of a reduced power RF current due to the concentration of energy at the ultra-sharp tip. Efficient cutting at lower power reduces blood loss and leads to much cleaner and less traumatic cuts, resulting in less scar tissue. Use of the ultra-sharp needle also eliminates the drag when cutting tissue. This "no-touch" technique allows the surgeon a sensitive "feel", which is a significant benefit when performing extreme microsurgery. When used in the cauterization mode, the ultra-sharp electrode may again be used at relatively lower RF power, thereby eliminating problems associated with excessive heat, such as melting the electrode needle, and with greater control over the direction and location of sparking.

Ultra-sharp refractory alloy needles are traditionally produced in two manners. In the glass blowing art, clean tungsten alloy surfaces of wires and plates are produced by etching the tungsten surface by contacting the hot tungsten with a solid bed of sodium nitrite. The resulting oxidation reaction leaves the tungsten clean and bright. In the electron microscopy art, the ultra-sharp tungsten needle used for the electron source in the electron gun is also produced by placing a direct electrical anodic voltage on the tungsten and emersing it in a concentrated aqueous sodium hydroxide solution. The etching away of the tungsten surface can be manipulated to create the tapered ultra-sharp tungsten needle.

This invention describes a unique method for producing ultra-sharp tungsten alloy needles by reaction in a molten solution of sodium nitrite. By following the method taught by this invention, ultra-sharp needles are produced having superior consistency, symmetry, sharpness and tapering, ideal for practicing the electrosurgical methods of this invention.

DRAWINGS

DESCRIPTION OF THE PREFERRED EMBODIMENTS

Figure 1:
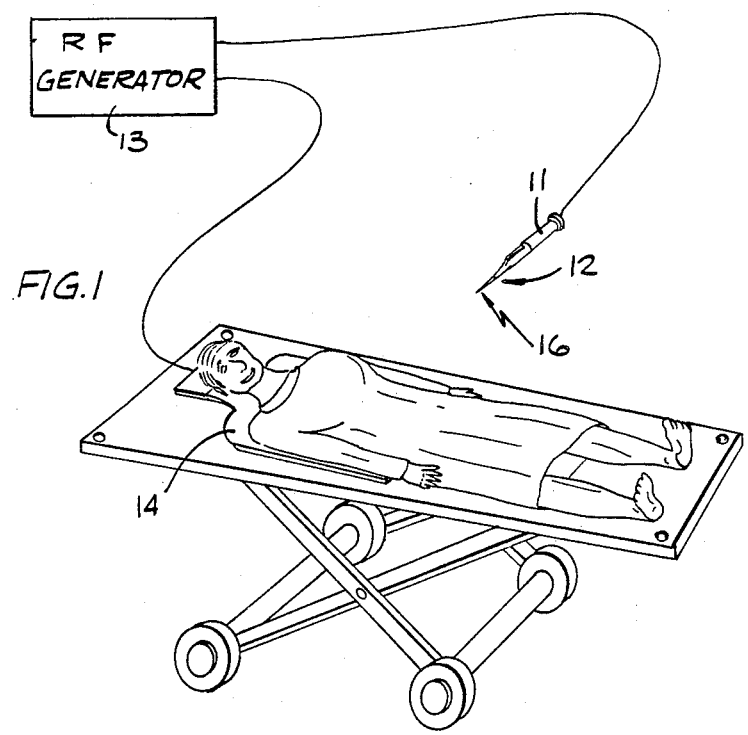
FIG. 1 is a perspective view of a monopolar electrosurgical device.

FIG. 1 shows a commonly used type of monopolar electrosurgical device. The holder device 11 connects the electrosurgical electrode 12 to the high frequency (RF) generator 13. A variety of holder devices may be employed. The holder devices are often equipped with useful features such as (1) a switch for selecting cutting mode or cauterizing mode power supply (2) a light for improved vision during electrosurgery and (3) a stream of inert gas to help coagulate blood during cutting, to blow away newly shed blood and to reduce the tendency of the hot electrode to oxidize.

The high frequency generator 13 is also connected to the patient plate 14. Generally, the patient plate is covered with an electroconductive gel, and the patient lies on the plate. When the high frequency generator is turned on, the circuit is not complete and no energy flow occurs until the current is allowed to flow between the electrode 12 and the patient plate 14, via the patient. The patient plate "grounds" the patient to the generator, receiving the high frequency current and completing the circuit back to the generator.

Figure 2:
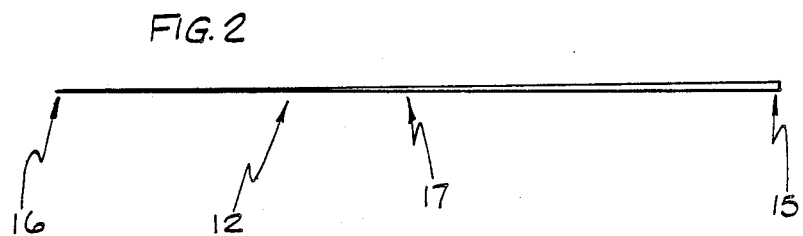
FIG. 2 is a side view of an ultra-sharp refractory alloy electrosurgical electrode.

FIG. 2 shows an electrosurgical electrode 12 of the type contemplated by this invention. The electrode 12 is composed of a refractory alloy. The term "refractory alloy" refers to a common classification of alloys in the field of metallurgy, used to describe a group of metal alloys that do not soften, weaken or change their shape unless heated to extremely high temperatures. The refractory alloys usually are based upon one or more metallic elements chosen from the list of tungsten, molybdenum, chromium, nickel, and cobalt. Preferably, the electrode is composed of a tungsten alloy. Most preferably, the electrode of the present invention is composed of a tungsten alloy containing at least 80% tungsten.

The electrosurgical electrode 12 has a blunt end 15 and a tip end 16. The tip end 16 is ultra-sharp. For the purposes of this invention, ultra-sharp is defined as a tip that is significantly sharper than can be obtained by normal mechanical tooling techniques.

Figure 3:
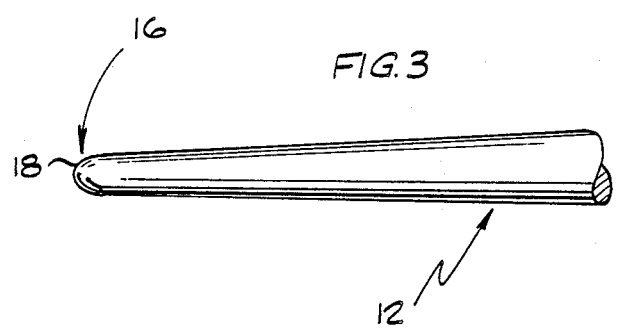
FIG. 3 is an expanded view of a portion of FIG. 2.

FIG. 3 shows a highly magnified view of the tip end 16 of an ultra-sharp electrosurgical electrode 12. Any sharp tip, when viewed at a high enough magnification, appears as a rounded hemisphere as is shown. The measure of sharpness of a tip is best expressed as the radius of the hemisphere, or the "tip radius," shown as line 18 in FIG. 3. The ultra-sharp tip 16 of the present invention has a tip radius 18 of less than 50 microns. Preferably, the ultra-sharp tip has a tip radius 18 of less than 10 microns, and in the most preferred embodiment, the tip radius 18 is less than one micron.

The electrosurgical electrodes currently available and those disclosed in the prior act are manufactured via mechanical means. The tip radius 18 of such an electrode would generally be of the order of 50 to 100 microns.

The electrosurgical electrode 12 may be of any length, and the diameter of the cylindrical electrode shaft at the blunt end 15 may be of any diameter capable of fitting into an electrosurgical electrode holder device 11. In one preferred embodiment of this invention, the electrode 12 is less than 55 mm long and greater than 20 mm long, and the diameter of the electrode shaft at the blunt end 15 is less than 0.05 inches. In an alternative embodiment, the electrode is greater than 50 cm long and the diameter is less than 0.02 inches.

In a preferred embodiment, the ultra-sharp electrode is tapered only throughout a portion of the length of the electrode. As can be seen in FIG. 2, the diameter of the cylindrical electrode 12 is constant from the blunt end 15 to some tapering point 17 between the blunt end 15 and the tip end 16. At this tapering point 17, the diameter of the electrode 12 is reduced generally consistently and proportionately to the tip end 16. For example, the diameter of the electrode at a position midway between the tapering point 17 and the tip end 16, would be approximately one half of the diameter at the blunt end 15. In the preferred embodiment, the tapering point 17 is 10–30 mm from the blunt end 15.

In another preferred embodiment of the invention, the ultra-sharp refractory alloy electrosurgical electrode 12 may be adapted for electrosurgery in conjunction with invasive cerebral endoscopy or other invasive surgical processes. In this embodiment, the electrode is approximately 20 inches long and the diameter at the blunt end 15 is less than 0.03 inches. In addition, the tapering point 17 is 0.5 to 2 mm from the tip end 16 and the electrode is electrically insulated by an adherent coating except for approximately 0.5 mm at the tip end.

Performing electrosurgery pursuant to this invention involves the following steps: (1) an electrosurgical holder, usually of the type shown in FIG. 1, is equipped with an electrosurgical electrode composed of a refractory alloy that has an ultra-sharp tip; (2) connecting the holder device to a high frequency (RF) generator which is also attached to a patient plate which is fastened securely to the skin of the patient; and (3) closely approaching or contacting the patient's body tissue with the needle electrode in order to complete the flow of energy and cut or cauterize body tissue.

By using the ultra-sharp electrode of this invention, the flow of energy from the electrode to the patients body becomes extremely concentrated. This concentration allows for the use of a reduced power RF current, a finer line of intense heat, less electrical sparking, thinner incisions, less scar tissue formation, and less blood loss. The concentration of intensity also provides the surgeon with a more delicate feel, enabling him to make extremely precise cuts without any friction or tearing.

The ultra-sharp electrosurgical electrode may also be used in a bipolar type of electrosurgical device (not shown). Such a method of electrosurgery would involve the following steps: (1) Equipping an electrosurgical holder device with at least one electrode composed of a refractory alloy and having ultra-sharp tips; (2) connecting the holder device to an appropriate radio frequency generator and (3) closely approaching or contacting a patient's body tissue with the electrodes in order to cut or cauterize the body tissue.

In utilizing ultra-sharp refractory alloy electrosurgical electrodes in bipolar electrosurgery, the only added requirement over conventional bipolar electrosurgical techniques is that at lest one ultra-sharp refractory alloy electrode be employed and that lower electrical power be used. In the method using a monopolar electrosurgical device, the electrode preferably has a blunt end and an ultra-sharp tip end. In a method using a bipolar electrosurgical device, the electrodes could take on any number of shapes.

The ultra-sharp tip required by the present invention is preferably produced by the following method: (1) a needle or rod of a refractory alloy is vertically held and dipped into a container holding a pool or bath of molten oxidizing agent, (2) at all times that the needle is in contact with the oxidizing agent, the needle is rotated about its own axis; and (3) withdrawing and replacing said needle into the pool of molten oxidizing agent at rates and distances which produce the desired tapering of the needle.

In a preferred embodiment of this method, the needle is composed of a tungsten alloy that, before sharpening, consists of a cylindrical rod of a consistent diameter that is less than 0.05 inches. The needle is turned at a constant speed of at least two revolutions per second throughout the oxidation/sharpening process. Preferably, the oxidizing agent employed is molten sodium nitrite. While rotating about its axis the whole time, the needle is repeatedly withdrawn from and replaced back into the molten pool. The tip end 16 of the needle spends the most time in contact with the oxidizing agent by following this procedure, and in time an ultra-sharp tip tapering up to the cylindrical diameter of the rod is formed.

The preferred oxidizing agent for performing the present procedure is sodium nitrite. However, it should be clear that any molten chemical compound capable of etching away the surface of the refractory alloy may be utilized. Other potential oxidizing agents are lithium, potassium, rubidium and cesium nitrite and lithium, potassium, rubidium, sodium or cesium nitrate.

When visual examination of the tip end of the needle indicates that the desired ultra-sharp tip has been formed, the needle should preferably be rinsed in water and then emersed in a bath of aqueous caustic solution in order to remove any traces of metal oxide from the surface of the needle. Preferably the caustic solution is aqueous concentrated sodium hydroxide.

In the most preferred embodiment of this method, the tungsten alloy needle is held in a drill-press device, whereby the needle may be rotated at a consistent speed and the needle may be raised and lowered smoothly. In this embodiment, solid sodium nitrite is placed in an insulated crucible which is equipped with heating coils. The heating coils are attached to an electrical power source, which is turned on in order to raise the temperature inside the crucible above the melting point of the sodium nitrite. Since the reaction between the oxidizing agent and the tungsten metal generates a substantial amount of heat, care must be taken to prevent spillage and excessive sputtering of the hot sodium nitrite. Following formation of the ultra-sharp tip, the crucible containing the sodium nitrite is replaced with a container of concentrated aqueous sodium hydroxide, and the needle is lowered into this solution. Upon cooling, a clean ultra-sharp electrosurgical electrode has been manufactured.

The foregoing description of the preferred embodiments of this invention are merely for the purposes of making an adequate disclosure of the invention. It would, however, be apparent to one skilled in the art that numerous changes in the details set forth above could be made while still falling within the bounds of this invention.

We claim:

1. An electrosurgical electrode composed of a refractory alloy comprising a solid needle with a blunt end and a tip end, the tip radius of said tip end being less than 50 microns.

2. The electrosurgical electrode of claim 1 composed primarily of a metal selected from the group consisting of tungsten, molybdenum, chromium, nickel and cobalt.

3. The electrosurgical electrode of claim 1 composed of a tungsten alloy containing at least 80% tungsten.

4. The electrosurgical electrode of claim 1 wherein the diameter of the needle is less than 0.05 inches at the blunt end.

5. The electrosurgical electrode of claim 4 wherein the distance between said tip end and said blunt end is between 20 mm and 55 mm.

6. The electrosurgical electrode of claim 5 wherein the diameter of said needle remains constant from said blunt end to a tapering point on said needle between 10 mm and 30 mm from said tip end, and between said tapering point and said tip end the diameter is consistently and proportionately reduced.

7. The electrosurgical electrode of claim 1 wherein the tip radius of said tip end is less than 10 microns.

8. The electrosurgical electrode of claim 1 wherein the tip radius of said tip end is less than one micron.

9. The electrosurgical electrode of claim 6 wherein the tip radius of said tip end is less than 10 microns.

10. The electrosurgical electrode of claim 1 wherein the diameter of the needle is less than 0.03 inches at the blunt end, the distance between said tip end and said blunt end is greater than 20 inches, and the tapering point is between 0.5 and 2 mm from said tip end.

11. The electrosurgical electrode of claim 10 composed of a tungsten alloy containing at least 80% tungsten.

12. An electrosurgical electrode composed of a refractory alloy comprising a solid needle with a blunt end and a tip end, the tip radius of said tip end being less than 50 microns, said blunt end having a diameter of less than 0.05 inches, wherein the distance between said tip end and said blunt end is between 20 mm and 55 mm, the diameter of said needle remains constant from said blunt end to a tapering point on said needle between 10 mm and 30 mm from said blunt end, and between said tapering point and said tip end the diameter is consistently and proportionately reduced.

13. The electrosurgical electrode of claim 12 composed of a tungsten alloy containing at least 80% tungsten.

* * * * *